(12) United States Patent
Chang et al.

(10) Patent No.: US 11,653,845 B2
(45) Date of Patent: May 23, 2023

(54) CONTINUOUS PHYSIOLOGICAL SENSING IN ENERGY-CONSTRAINED WEARABLES

(71) Applicant: INTERNATIONAL BUSINESS MACHINES CORPORATION, Armonk, NY (US)

(72) Inventors: Hung-Yang Chang, Scarsdale, NY (US); Tian Hao, White Plains, NY (US); Xinxin Zhu, Croton on Hudson, NY (US)

(73) Assignee: International Business Machines Corporation, Armonk, NY (US)

( * ) Notice: Subject to any disclaimer, the term of this patent is extended or adjusted under 35 U.S.C. 154(b) by 450 days.

(21) Appl. No.: 15/794,329

(22) Filed: Oct. 26, 2017

(65) Prior Publication Data

US 2019/0130076 A1    May 2, 2019

(51) Int. Cl.
*A61B 5/024* (2006.01)
*A61B 5/11* (2006.01)
(Continued)

(52) U.S. Cl.
CPC ........ *A61B 5/02416* (2013.01); *A61B 5/0022* (2013.01); *A61B 5/0205* (2013.01);
(Continued)

(58) Field of Classification Search
CPC ... G06F 19/3418; A61B 5/11; A61B 5/02416; A61B 5/0205; A61B 5/0022;
(Continued)

(56) References Cited

U.S. PATENT DOCUMENTS 8,159,333 B2    4/2012    Huang et al.
8,630,222 B2    1/2014    Wang et al.
(Continued)

FOREIGN PATENT DOCUMENTS

CN    105266776 A    1/2016
CN    106647945 A    5/2017
(Continued)

OTHER PUBLICATIONS

Bandyopadhyay, Seema et al. "An Energy Efficient Hierarchical Clustering Algorithm for Wireless Sensor Networks", School of Electrical and Computer Engineering-Purdue University, 2003, pp. 1-11.

(Continued)

*Primary Examiner* — John P Go
*Assistant Examiner* — Chad A Newton
(74) *Attorney, Agent, or Firm* — Cantor Colburn LLP; Kristofer Haggerty

(57) ABSTRACT

Embodiments of the present invention are directed to physiological sensing in a wearable device. Aspects include generating a multi-faceted feedback for a user. Generating the multi-faceted feedback includes generating a baseline physiological sampling schedule for a user, generating a quality-aware feedback of the user, generating a user-state-aware feedback of the user, and generating a context-aware feedback of the user. Aspects also include generating an adjusted physiological sampling schedule for the user based at least in part upon the multi-faceted feedback.

15 Claims, 10 Drawing Sheets

(51) Int. Cl.
  *A61B 5/0205* (2006.01)
  *G16H 50/30* (2018.01)
  *G16H 40/63* (2018.01)
  *A61B 5/00* (2006.01)
  *G06Q 10/1093* (2023.01)

(52) U.S. Cl.
  CPC .............. *A61B 5/11* (2013.01); *A61B 5/486* (2013.01); *A61B 5/681* (2013.01); *A61B 5/721* (2013.01); *G06Q 10/1093* (2013.01); *G16H 40/63* (2018.01); *G16H 50/30* (2018.01); *A61B 2560/0209* (2013.01); *A61B 2562/0219* (2013.01)

(58) Field of Classification Search
  CPC ......... A61B 5/486; A61B 5/681; A61B 5/721; A61B 2560/0209; A61B 2562/0219; G16H 50/30; G16H 40/63; G06Q 10/1093
  See application file for complete search history.

(56) References Cited

U.S. PATENT DOCUMENTS

| | | | |
|---|---|---|---|
| 8,706,172 | B2 | 4/2014 | Priyantha et al. |
| 8,849,325 | B2 | 9/2014 | Schreiber et al. |
| 9,237,855 | B2 | 1/2016 | Hong et al. |
| 9,572,533 | B2 | 2/2017 | Venkatraman et al. |
| 10,154,460 | B1* | 12/2018 | Miller ................ A61B 5/14546 |
| 2008/0058616 | A1 | 3/2008 | Nakagawa et al. |
| 2012/0268249 | A1 | 10/2012 | Kansal et al. |
| 2012/0283524 | A1* | 11/2012 | Kiani ................ A61B 5/14551 600/301 |
| 2014/0275852 | A1* | 9/2014 | Hong .................. A61B 5/0002 600/479 |
| 2015/0185819 | A1 | 7/2015 | Saito |
| 2015/0318738 | A1 | 11/2015 | Pan |
| 2016/0029964 | A1* | 2/2016 | LeBoeuf .............. A61B 5/4266 600/476 |
| 2017/0071546 | A1 | 3/2017 | Jain et al. |
| 2017/0181630 | A1* | 6/2017 | Mahalingam .......... A61B 5/746 |
| 2019/0008437 | A1* | 1/2019 | Ben-Ezra ............. G06K 9/6289 |

FOREIGN PATENT DOCUMENTS

| | | |
|---|---|---|
| CN | 106774861 A | 5/2017 |
| JP | 2004129905 A | 4/2004 |
| JP | 2006141902 A | 6/2006 |
| JP | 2008061663 A | 3/2008 |
| JP | 2015123300 A | 7/2015 |
| WO | 2016103198 A1 | 6/2016 |

OTHER PUBLICATIONS

Kang, Seungwoo et al. "SeeMon: Scalable and Energy-efficient Context Monitoring Framework for Sensor-rich Mobile Environments", 2008, http://ink.library.smu.edu.sg/sis_research/2072.

He, Tian et al. "VigilNet: an Integrated Sensor Network System for Energy-Efficient Surveillance", Department of Electrical and Computer Engineering-Carnegie-Mellon University, 2005.

Mamaghanian, Hossein et al. "Compressed Sensing for Real-Time Energy-Efficient ECG Compression on Wireless Body Sensor Nodes", IEEE Transactions on Biomedical Engineering, vol. 58, No. 9, 2011, pp. 2456-2466.

Wang, Yi et al. "A Framework of Energy Efficient Mobile Sensing for Automatic User State Recognition", Ming Hsieh Department of Electrical Engineering-University of Southern California, 2009.

Ye, Wei et al. "An Energy-Efficient MAC Protocol for Wireless Sensor Networks", Wireless Sensor Network, vol. 1, No. 1-69, 2008. pp. 59-69.

Notification of Transmittal of the International Search Report and the Written Opinion of the International Searching Authority, or the Declaration, issued in International Application No. PCT/IB2018/058231, dated Feb. 13, 2019; 9 pages.

International Office Action; Japanese Patent Application No. 2020-519760; International Filing Date: Oct. 23, 2018; dated Jun. 20, 2022; 3 pages.

International Office Action; International Application No. 2020-519760; International Filing Date: Oct. 23, 2018; dated Feb. 22, 2022; 6 pages.

* cited by examiner

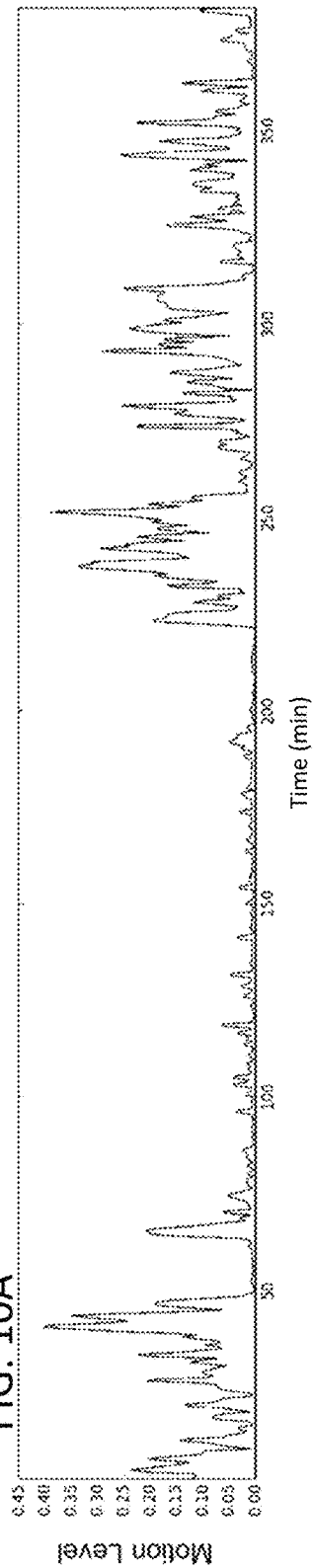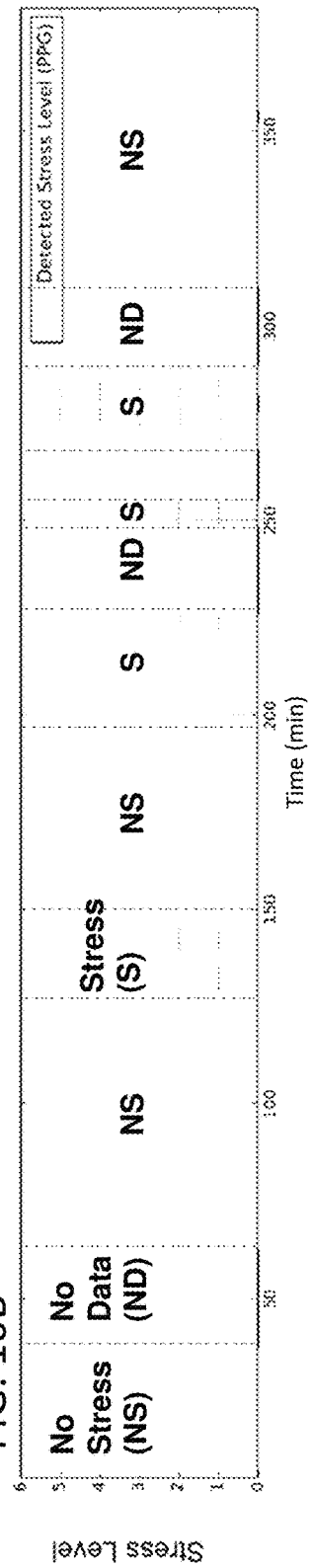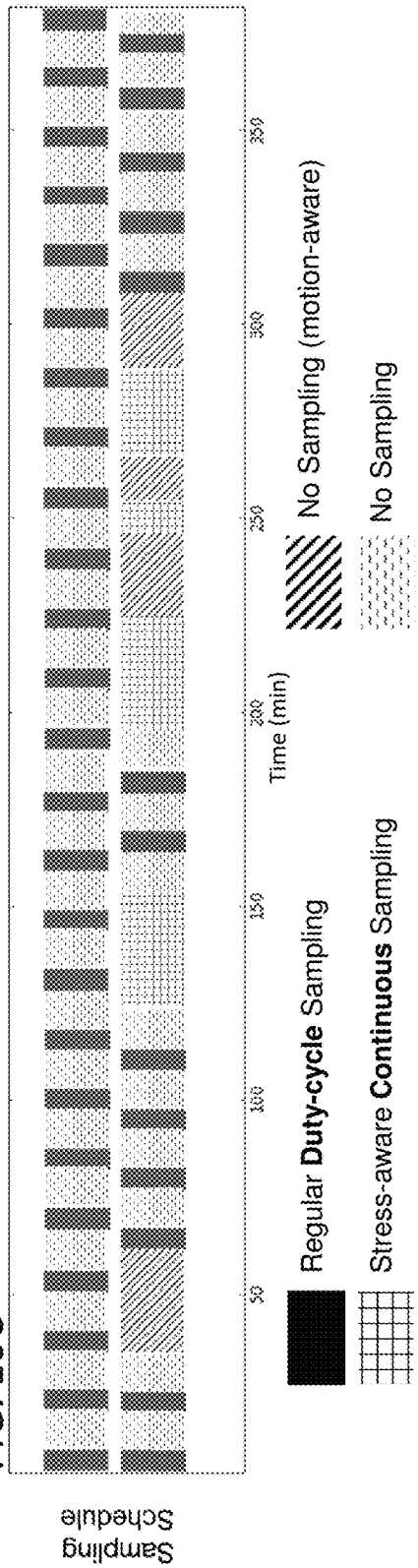

CONTINUOUS PHYSIOLOGICAL SENSING IN ENERGY-CONSTRAINED WEARABLES

BACKGROUND

The present invention relates in general to physiological sensing and, more specifically, to continuous physiological sensing in energy-constrained wearables.

Precision medicine and precision health care can customize care and treatment to an individual patient based upon personized factors and individual characteristics, such as environment and lifestyle as well as genetic and cellular characteristics. Precision health management can call for continuous physiological sensing. By obtaining continuous and real-time information, rather than snap shots of information as are obtained through conventional in office physical examinations for example, timely and accurate information can be obtained. Such continuous and real-time information can be valuable in health care contexts because it enables systems and users to take proactive actions with precision and allows rapid intervention in times of need. A number of physiological sensors, such as heart rate monitors, have been implemented on wearable devices that are available to consumers at large, such as smart watches.

SUMMARY

Embodiments of the present invention are directed to a processing system for physiological sensing in a wearable device. The processing system can include a processor in communication with one or more types of memory. The processor is configured to generate a multi-faceted feedback for a user. Generating the multi-faceted feedback includes generating a baseline physiological sampling schedule for a user, generating a quality-aware feedback of the user, generating a user-state-aware feedback of the user, and generating a context-aware feedback of the user. The processor is also configured to generate an adjusted physiological sampling schedule for the user based at least in part upon the multi-faceted feedback.

Embodiments of the present invention are directed to a computer-implemented method for physiological sensing in a wearable device. The method includes generating a multi-faceted feedback for a user. The method includes generating a baseline physiological sampling schedule for a user. The method also includes generating a quality-aware feedback of the user. The method also includes generating a user-state-aware feedback of the user. The method also includes generating a context-aware feedback of the user. The method also includes generating an adjusted physiological sampling schedule for the user based at least in part upon the multi-faceted feedback.

Embodiments of the invention are directed to a computer program product for physiological sensing in a wearable device. The computer program product includes a computer readable storage medium having program instructions embodied therewith. The instructions are executable by a processor to cause the processor to perform a method. The method includes generating a multi-faceted feedback for a user. The method includes generating a baseline physiological sampling schedule for a user. The method also includes generating a quality-aware feedback of the user. The method also includes generating a user-state-aware feedback of the user. The method also includes generating a context-aware feedback of the user. The method also includes generating an adjusted physiological sampling schedule for the user based at least in part upon the multi-faceted feedback.

Embodiments of the invention are directed to a system for physiological sensing in a wearable device. The system includes a multi-faceted sampling regulation center. The multi-faceted sampling regulation center includes a user-state aware feedback module; a context-aware feedback module; a quality aware feedback module; and a sampling regulator. The system also includes a plurality of sensors. The system also includes a user interface.

Embodiments of the invention are directed to a system for physiological sensing in a wearable device. The system includes a sampling regulation center in communication with a context synthesizer. The system also includes an always-on interference assessment module. The system also includes a physiological state sensing module.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIG. 10A depicts aspects of an exemplary system according to embodiments of the present invention.

FIG. 10B depicts aspects of an exemplary system according to embodiments of the present invention.

FIG. 10C depicts aspects of an exemplary system according to embodiments of the present invention.

Figure 1:
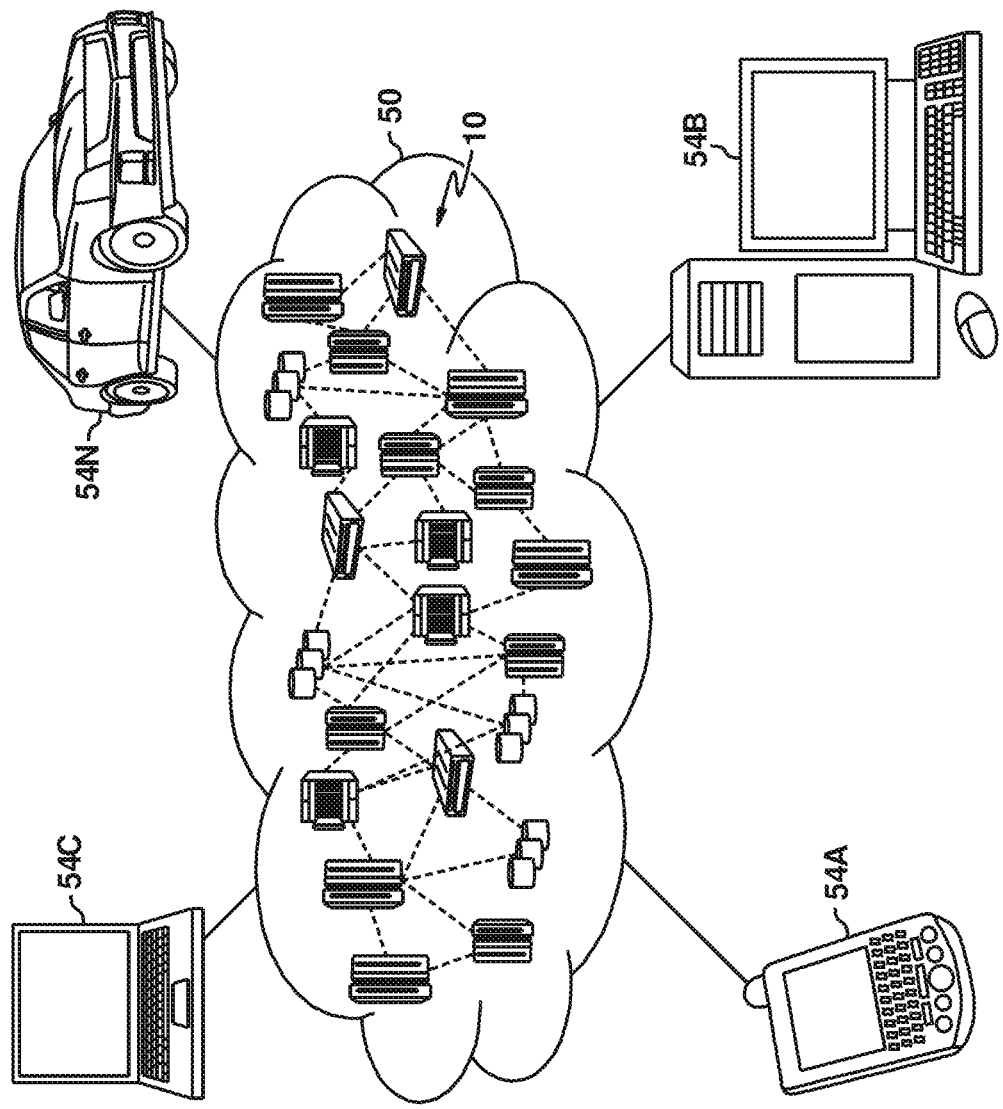
FIG. 1 depicts a cloud computing environment according to embodiments of the present invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the described embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" can be understood to include any integer number greater than or equal to one, i.e. one, two, three, four, etc. The terms "a plurality" can be understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
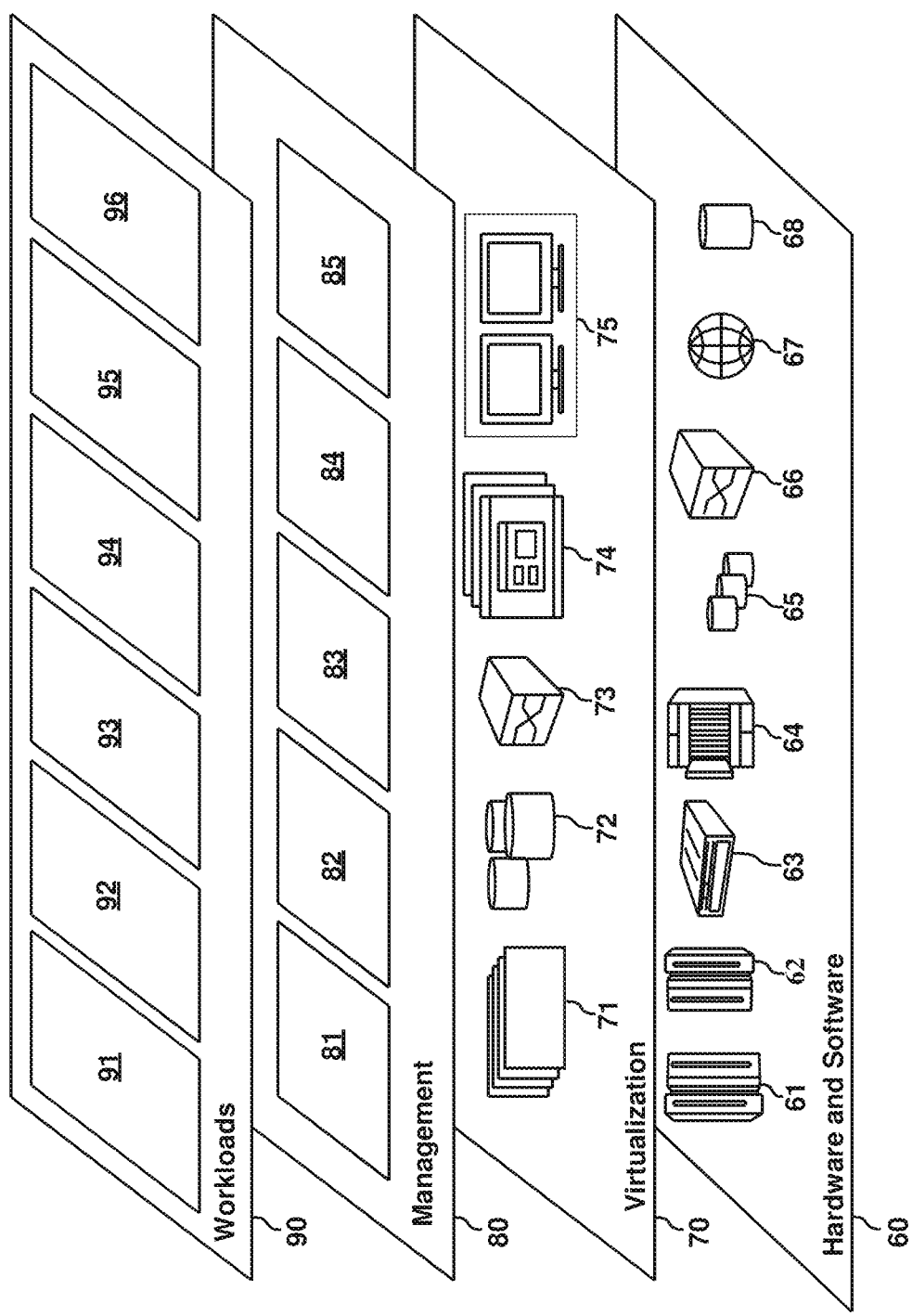
FIG. 2 depicts abstraction model layers according to embodiments of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments of the invention, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and physiological sensing 96.

Figure 3:
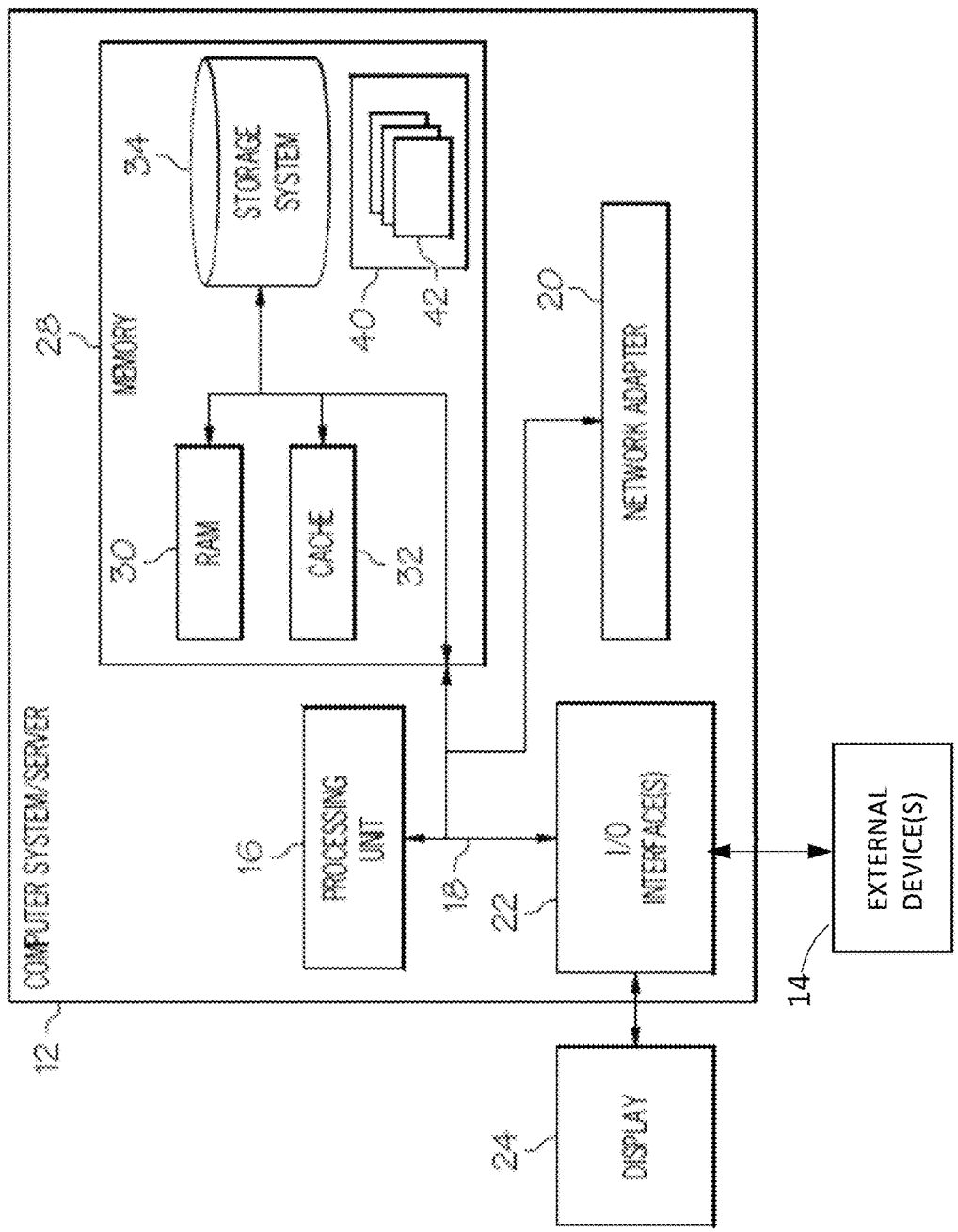
FIG. 3 depicts a computer system according to embodiments of the present invention.

Referring now to FIG. 3, a schematic of a cloud computing node 100 included in a distributed cloud environment or cloud service network is shown according to a non-limiting embodiment. The cloud computing node 100 is only one example of a suitable cloud computing node and is not intended to suggest any limitation as to the scope of use or functionality of embodiments of the invention described herein. Regardless, cloud computing node 100 is capable of being implemented and/or performing any of the functionality set forth hereinabove.

In cloud computing node 100 there is a computer system/server 12, which is operational with numerous other general purpose or special purpose computing system environments or configurations. Examples of well-known computing systems, environments, and/or configurations that can be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 can be described in the general context of computer system-executable instructions, such as program modules, being executed by a computer system. Generally, program modules can include routines, programs, objects, components, logic, data structures, and so on that perform particular tasks or implement particular abstract data types. Computer system/server 12 can be practiced in distributed cloud computing environments where tasks are performed by remote processing devices that are linked through a communications network. In a distributed cloud computing environment, program modules can be located in both local and remote computer system storage media including memory storage devices.

As shown in FIG. 3, computer system/server 12 in cloud computing node 100 is shown in the form of a general-purpose computing device. The components of computer system/server 12 can include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out the functions and/or methodologies of embodiments of the invention as described herein.

Computer system/server 12 can also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Turning now to an overview of technologies that are more specifically relevant to aspects of the invention, precision health management is desirable for its potential to provide proactive and timely care to patients. Precision health management can call for continuous physiological sensing, such as the sensing of heart rate, blood pressure, motion related data, and the like.

A number of physiological sensors have been implemented in consumer wearable devices. Inclusion of such sensors in consumer wearable devices can be desirable because such devices are increasingly user-friendly in that they are light weight, relatively small and discrete, and because such devices can perform multiple functions, such as internet connectivity, scheduling, and communication activities, reducing the number and cost associated that would be associated with individualized components. For example, a smart watch can include a heart rate sensor and various positioning related components, such as accelerometers, global positioning systems, and gyrometers.

Although physiological sensing components are small enough to be able to be included in small wearable devices, the scarcity of power in wearable devices renders continuous sensing impractical. Because wearable devices are size and weight limited, components and functionalities of wearable devices must compete for a limited supply of power. For instance, certain physiological sensors, such as heart rate monitors, have a relatively high power consumption, placing practical limits on real-time and continuous sampling. By way of example, continuously sampling (25 Herz) with a photoplethysmography (PPG) heart rate sensor can consume ten to fifteen percent of a MOTOROLA™ Moto 360 smartwatch battery per hour of use.

Current multi-function devices, such as smartwatches, that perform physiological sensing manage power consumption issues by using fixed, timer-based scheduling. For example, a smart watch with a heart rate monitor can be set to sample for ten seconds out of every ten minutes. Moreover, with respect to physiological monitoring, such devices can be limited to heart rate monitoring, despite the availability of other relatively small physiological sensors.

Available wearable physiological sensors lack a sampling regulation mechanism that can reduce the sampling overhead in order to support continuous physiological sensing for precision health management.

Turning now to an overview of the aspects of the invention, one or more embodiments of the invention address the above-described shortcomings of the prior art by providing multi-faceted feedback to reduce energy consumption of sensors in wearable devices in physiological sensing applications to provide effectively continuous physiological sensing for precision health management. Embodiments of the invention use multi-faceted feedback to provide long-term physiological sensing with a high degree of temporal coverage and relatively low energy consumption. Multi-faceted feedback architecture according to embodiments of the invention can significantly reduce power consumption of wearable devices while maintaining satisfactory sensing performance.

The above-described aspects of the invention address the shortcomings of the prior art by adjusting the sampling schedule and active sensors in wearable devices based upon data quality, a user's physiological state, context, and power usage. Embodiments of the invention can selectively sample during physiologically relevant time periods, as determined for instance by user state and contextual cues, and during time periods that are unlikely to yield a lack of relevant data due to quality issues, such as excess noise. Systems according to embodiments of the invention include quality aware feedback, such as interference levels, user-state aware feedback, such as physiological state data, context-aware feedback, such as context data, and optionally energy-aware feedback, such as power usage policy data, to regulate sampling for optimal energy consumption. Multi-faceted feedback according to embodiments of the invention can significantly preserve device energy consumption by providing adaptive adjustment of the sampling schedule based upon data quality, user's physiological state, context, and power usage.

Embodiments of the invention enable continuous physiological sensing on wearable devices. The multi-faceted feedback systems according to embodiments of the invention can reduce unnecessary and energy-expensive sampling, make the most optimal use of restrained energy, and/or maintain a balance between prolonged battery life and satisfactory sensing results. Embodiments of the invention make it practical for wearable devices to obtain a user's real-time physiological state, allowing proactive, precision delivery of health solutions and services.

Figure 4:
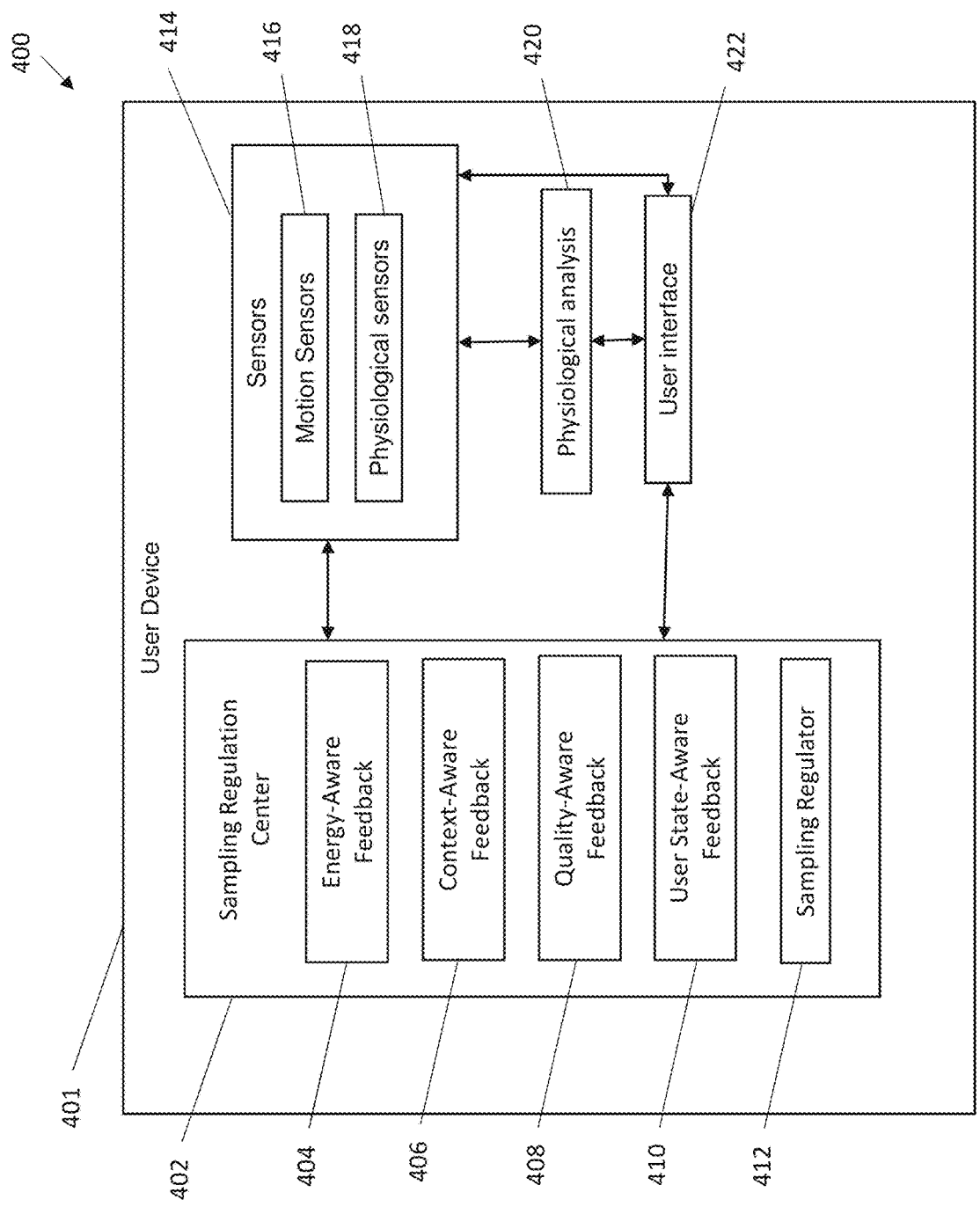
FIG. 4 depicts aspects of an exemplary system according to embodiments of the present invention.

Turning now to a more detailed description of aspects of the invention, FIG. 4 depicts aspects of an exemplary system 400 according to embodiments of the present invention. The system 400 can include a user device 401, such as a commercially available wearable technology, such as a smart watch, or a custom user device 401, such as an arm band, wrist band, head band, eye wear, or jewelry, such as rings or necklaces, and the like, adapted for physiological monitoring. The user device 401 can include a sampling regulation center 402 in communication with a plurality of sensors 414, including one or more motion sensors 416 and one or more physiological sensors 418. The sampling regulation center 402 can receive data from the sensors in some embodiments of the invention. In some embodiments of the invention, the sampling regulation center 402 can schedule or regulate the acquisition of data from one or more of the sensors 414. The sampling regulation center 402 can include a sampling regulator 412 that receives and interprets multi-faceted feedback from a plurality of modules, including a user-state aware feedback module 410, a quality-aware feedback module 408, a context-aware feedback module 406, and optionally an energy-aware feedback module 404. In some embodiments of the invention, the user device 401 can include a user interface 422. When present, a user interface 422 can be in communication with one or more system components, such as a sampling regulation center 402, a plurality of sensors 414, and/or a physiological analysis module 420.

The motion sensor 416 can include, for instance, an accelerometer, a gyroscope or a global positioning device. In some embodiments of the invention, the motion sensor 416 is a low-power sensor, i.e., a sensor with a relatively low power consumption profile such that it can remain active for several hours continuously without adversely affecting device performance, such as an accelerometer. In some embodiments of the invention, the motion sensor 416 operates continuously.

The motion sensor 416 can provide data to the quality-aware feedback module 408, for instance, to prevent the system from physiological sampling when high interference levels are detected. For example, high levels of movement can be determined by a motion sensor 416 and can lead to elevated vital signs, such as heart rate and respiration rate, in the absence of a physiological event for which the user is being monitored. For example, running or brisk walking can raise heart rate and respiration rate. Such elevations can interfere with certain types of physiological monitoring, which look, for example, for elevated or irregular vital signs as an indication of a physiological event, such as a stressful event in stress monitoring. The quality-aware feedback module 408 can estimate a level of interference based at least in part upon motion sensor data and can reduce or discontinue operation of physiological sensors if the level of interference exceeds a quality threshold. The quality threshold can be a level above which physiological sensor data is likely to lead to corrupted or unusable data.

Physiological sensors 418 can include any wearable sensors useful for detecting or predicting a physiological state of a user, such as heart rate monitors or sensors, temperature sensors, skin conductance sensors, optical or electrochemical biosensors, blood pressure monitors, blood oxygen saturation sensors, and/or respiratory sensors such as respiration rate sensors.

Physiological sensors 418 can provide data for the user state-aware feedback module 410 in some embodiments of the invention. The user state-aware feedback module 410 can adjust a sampling frequency based upon the intensity and frequency of recently detected user states. For instance, in the case of stress monitoring, if a recent sampling or test result indicates a user has been in a stressful state, the sampling frequency can be increased. Conversely, if a user has been in a stressful state with relatively high frequency monitoring, the user-state aware feedback module 410 can decrease the sampling frequency when the system receives an indication, for instance from physiological sensors or manual user input, that indicates a user is no longer in a stressful state.

In some embodiments of the invention, a user state-aware feedback module 406 can compare a user state to a baseline model for determining a relevant user state, for example based upon historical events of the user, based upon baseline physiological data for the user, based upon historical events or baseline physiological data for other users, such as users from a same or similar demographic group or with a shared or common health condition or health status.

Physiological sensors 416 can interact with a physiological analysis module 420, which can determine a user state based at least in part upon physiological sensor data. In some embodiments of the invention, physiological analysis module 420 can determine the presence of one or more user states by comparison to a baseline model. The physiological analysis module 420 can be located within the user device 401 in some embodiments of the invention. In some embodiments of the invention, not shown, a physiological analysis module is external to the user device 401, for instance, on a computer or tablet in communication with the user device or, for instance, in a cloud environment.

A context-aware feedback module 406 can allow the system 400 to proactively make energy-efficient adjustments according to contextual data, for instance from the user's historical physiological analysis results under certain contexts. For example, in the case of stress sensing, the context-aware feedback module can increase physiological sampling when the user is in a historically stressful context, such as at a client meeting. The context-aware feedback module 406 can obtain contextual data from the wearable device or from sources external to the wearable device, for instance, from calendar or email data, from global positioning or other location data, from accelerometer data (for instance in the case of an airplane take-off or landing), from the Internet, such as app-based weather data, traffic reports, and the like. In some embodiments of the invention, a context-aware feedback module 406 can generate a baseline model for determining a relevant contextual state, for example based upon locations or activities.

An energy-aware feedback module 404 can, in some embodiments of the invention, provide intelligent adjustment of sampling duty cycles according to current and projected power usage and/or based upon user preference regarding energy expenditure (e.g., aggressive or conservative power-use modes).

Figure 5:
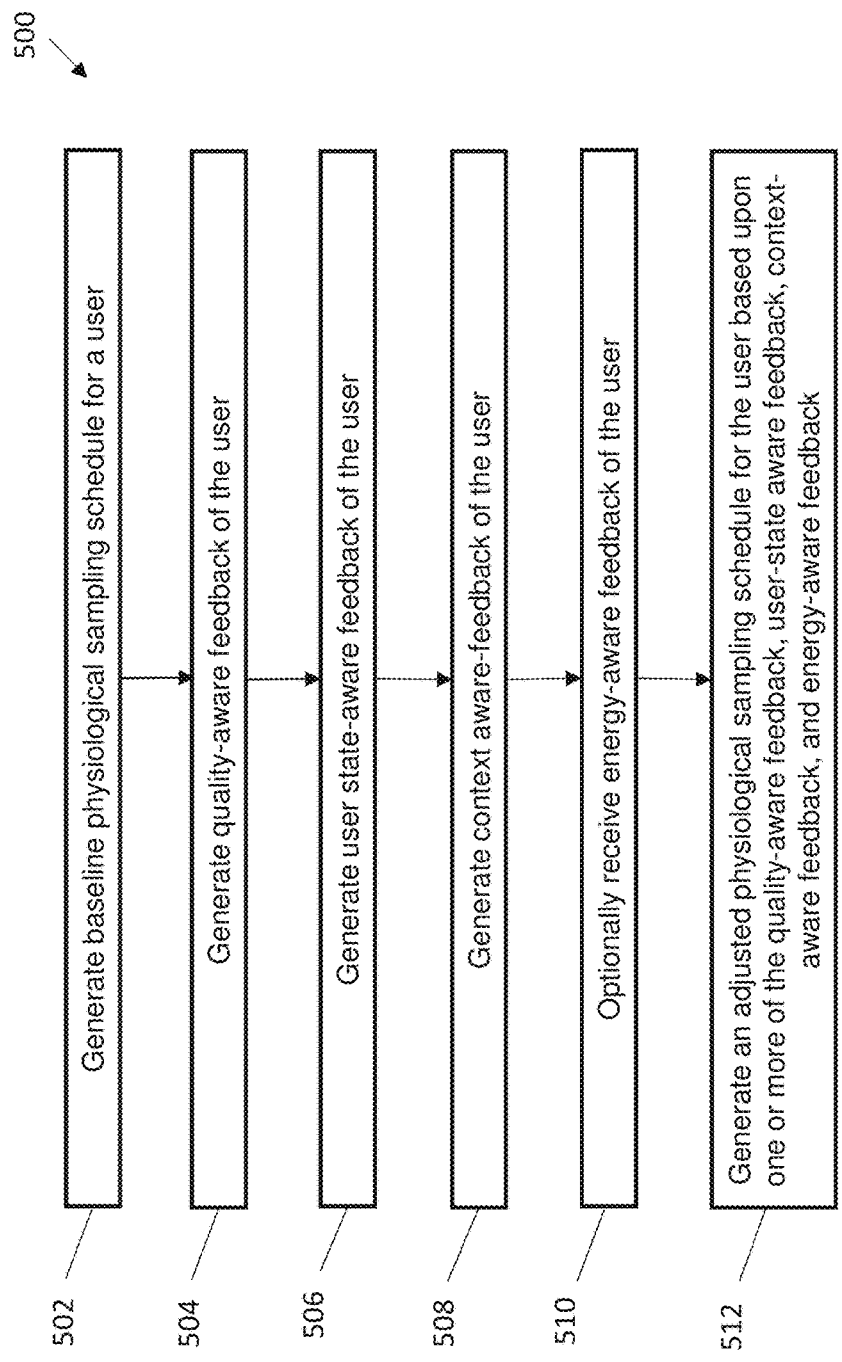
FIG. 5 depicts a flow diagram illustrating an exemplary method according to embodiments of the present invention.

FIG. 5 depicts a flow diagram illustrating an exemplary method 500 according to embodiments of the present invention. The method 500 can include, as shown at block 502, generating a baseline physiological sampling schedule of a user. The method 500 can also include, as shown at block 504, generating quality-aware feedback of the user. The method 500 can also include, as shown at block 506, generating user state-aware feedback of the user. The method 500 can also include, as shown at block 508, generating context-aware feedback of the user. The method 500 can also include, as shown at block 510, optionally receiving energy-aware feedback of the user. The method 500 can also include, as shown at block 512, adjusting the baseline physiological sampling schedule for the user based upon one or more of the quality aware feedback, user state-aware feedback, context-aware feedback, and energy-aware feedback.

Figure 6:
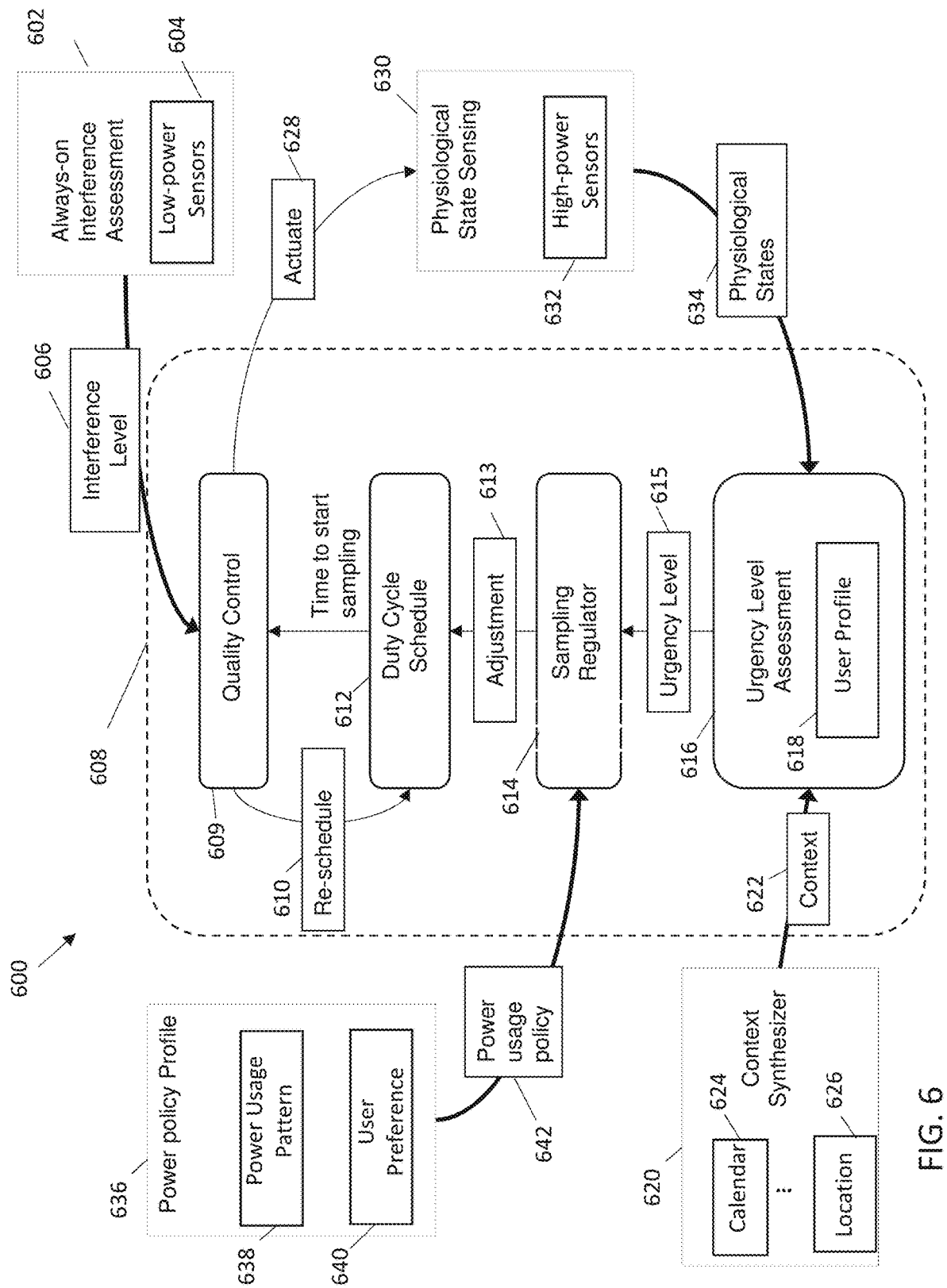
FIG. 6 depicts aspects of an exemplary system according to embodiments of the present invention.

FIG. 6 depicts aspects of an exemplary system 600 according to embodiments of the present invention. The exemplary system can include a sampling regulation center 608 in communication with a power policy profile module 636, a context synthesizer 620, an always-on interference assessment module 602, and a physiological state sensing module 630.

The always-on interference assessment module 602 can include one or more low-power sensors 604, such as accelerometers or gyroscopes and can output an interference level 606 to the sampling regulation center 608, for instance to a quality control module 609 in the sampling regulation center 608. In some embodiments of the invention, the always-on interference assessment module 602 and quality control module 609 are components of a quality-aware feedback system.

The sampling regulation center 608 can communicate with the physiological state sensing module 630, for instance by providing an actuate signal 628 to the physiological state sensing module 630. The physiological state sensing module 630 can include one or more physiological sensors, including high-power sensors 632, such as heart rate monitors. The physiological state sensing module, in some embodiments of the invention, can provide physiological states 634 to the sampling regulation center 608, for instance to an urgency level assessment module 616. The physiological state sensing module 630 can be a component of a user-state aware feedback system.

The context synthesizer 620 can include systems and components for determining a context, such as a calendar 624 and/or a location identifier 626, and can output a context 622 to the sampling regulation center 608, for instance to the urgency level assessment module 616.

The urgency level assessment module 616 can contain a user profile 618 including baseline information, such as baseline state information and baseline context information.

The urgency level assessment module can perform a user-state urgency determination to generate $U_{state}$, for example by integrating the intensity of recent physiological states at a time of X minutes from a current time T as follows:

$$U_{state} = \frac{\int_{T-X}^{T} \text{Intensity (state)} dt}{\text{Baseline}_{State}}$$

in which the sensitivity can be adjusted by changing X and $\text{Baseline}_{state}$.

The urgency level assessment module can perform a context-state-based urgency determination to generate $U_{context}$ as follows:

$$U_{context} = \frac{\text{Likelihood (context)}}{\text{Baseline}_{context}}$$

A context-based urgency determination is based upon the likelihood of occurrence of relevant physiological events obtained or derived from the user profile 618. The sensitivity of the context-based urgency determination can be adjusted by changing $\text{Baseline}_{context}$.

In some embodiments of the invention an urgency level 615 including an overall urgency estimation $U_{overall}$ can be generated based upon $U_{state}$ and $U_{context}$ by performing a rule-based fusion according to known techniques (e.g., Max ($U_{state}$, $U_{context}$)).

Baseline information, including $\text{Baseline}_{context}$ and $\text{Baseline}_{state}$ can be generated, for instance, in a learning stage based upon user labeling and/or machine learning. In some embodiments of the invention, baseline information is established in a hybrid learning phase based upon user labeling and machine learning techniques. Baseline information can, in some embodiments of the invention, be generated at least in part based upon information gathered from sources included within a wearable device, such as calendars, clocks, email, voice messages, maps, and the like. In some embodiments of the invention, baseline information is generated at least in part based upon data external to a wearable device, for instance data obtained from global positioning systems, external components linked to the wearable device via Bluetooth, WI-Fi, or near field communication (NFC), or cloud-based systems. In some embodiments of the invention, an urgency level 615 is provided to a sampling regulator 614.

In some embodiments of the invention, a power policy profile 636 includes a power usage pattern 638 and/or user preference 640 regarding power consumption. The power policy profile 636 can send a power usage policy 642 to the sampling regulator 614.

The sampling regulator 614 can reduce unnecessary sampling, for instance by decreasing the sampling frequency when an urgency level is low and increasing the sampling frequency when the urgency level is high. The sampling regulator 614 can maximize the number of potentially relevant captured events within desired energy constraints. For example, a power usage policy 642 can include rankings of aggressive, conservative, and automatic based upon user preferences. In some embodiments of the invention, a sampling regulator 614 can generate or perform a duty cycle adjustment 613 based at least in part upon the urgency level 615 and the power usage policy 642. For instance, the sampling regulator 614 can use a fuzzy-logic based controller including a plurality of rules, for example as follows:

FuzzyRule1 (Power, Urgency)
FuzzyRule2 (Power, Urgency)
FuzzyRule3 (Power, Urgency)

A duty cycle schedule 612 can be included within the sampling regulation center 608. The duty cycle schedule 612 can be adjusted by the sampling regulator 614 and/or receive a re-schedule 610 instruction from the quality control module 609. The duty cycle schedule 612 can provide times to start and stop physiological sensing.

Figure 7:
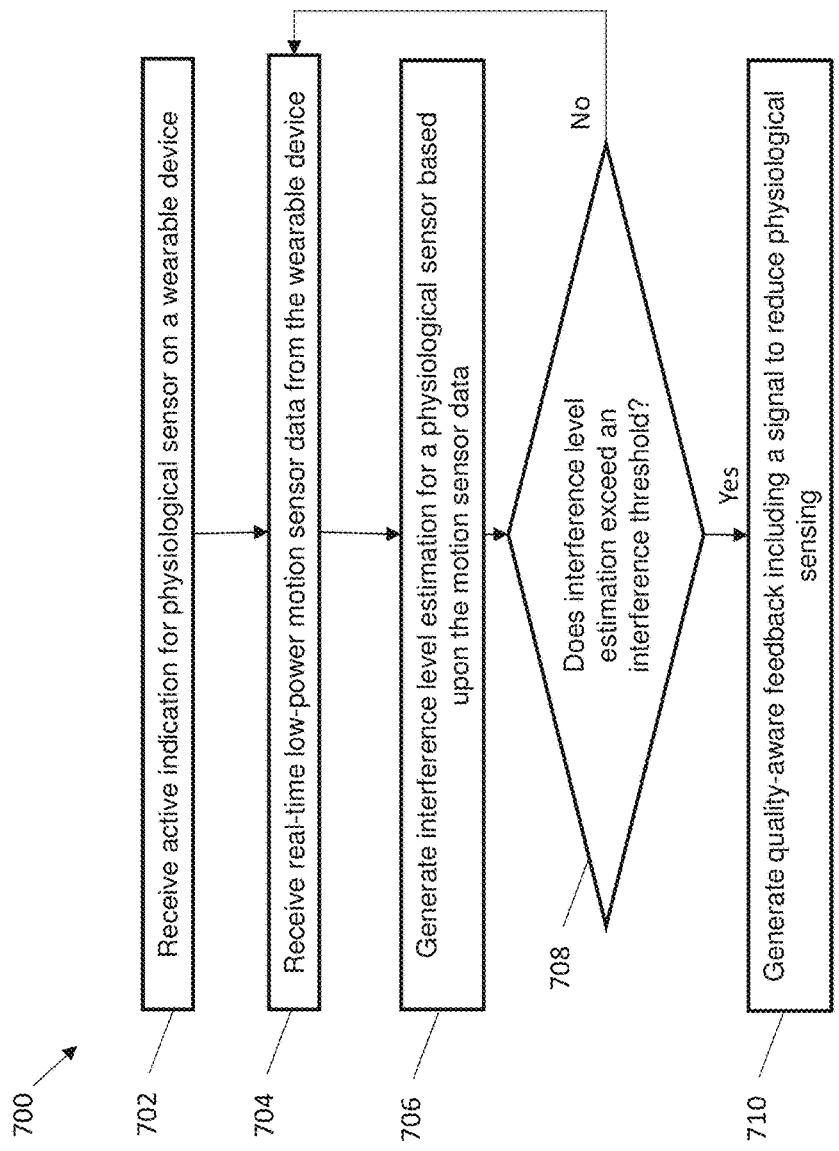
FIG. 7 depicts a flow diagram illustrating an exemplary method according to embodiments of the present invention.

FIG. 7 depicts a flow diagram illustrating an exemplary method 700 for generating a quality-aware feedback according to embodiments of the present invention. The method 700 includes, as shown at block 702, receiving an active indication for a physiological sensor on a wearable device. The active indication can be, for example, a signal indicating that one or more physiological sensors is in an active state. The method 700 can also include, as shown at block 704, receiving a real-time low-power motion sensor data from the wearable device. The real-time low-power motion sensor data can, for example, include accelerometer data from an always on accelerometer. The method 700 can also include, as shown at block 706, generating an interference level estimation for a physiological sensor based upon the motion sensor data. The interference level estimation can include a determination that user motion, sensed by the motion sensor, is likely to interfere with a physiological sensing application and generate corrupted, unreliable, or otherwise unusable physiological measurements. As shown at decision block 708, the method 700 asks whether the interference level estimation exceeds an interference threshold. Responsive to a determination that the interference level does not exceed an interference threshold, the method 700 can return to block 704. Responsive to a determination that the interference level estimation exceeds an interference threshold, the method 700 can generate a quality-aware feedback including a signal to reduce physiological sensing, as shown at block 710. The signal to reduce physiological sensing can include a directive to cease, postpone, or reduce a sampling frequency of physiological sensing. In some embodiments of the invention, the signal to reduce physiological sensing includes a directive to postpone physiological sensing.

Figure 8:
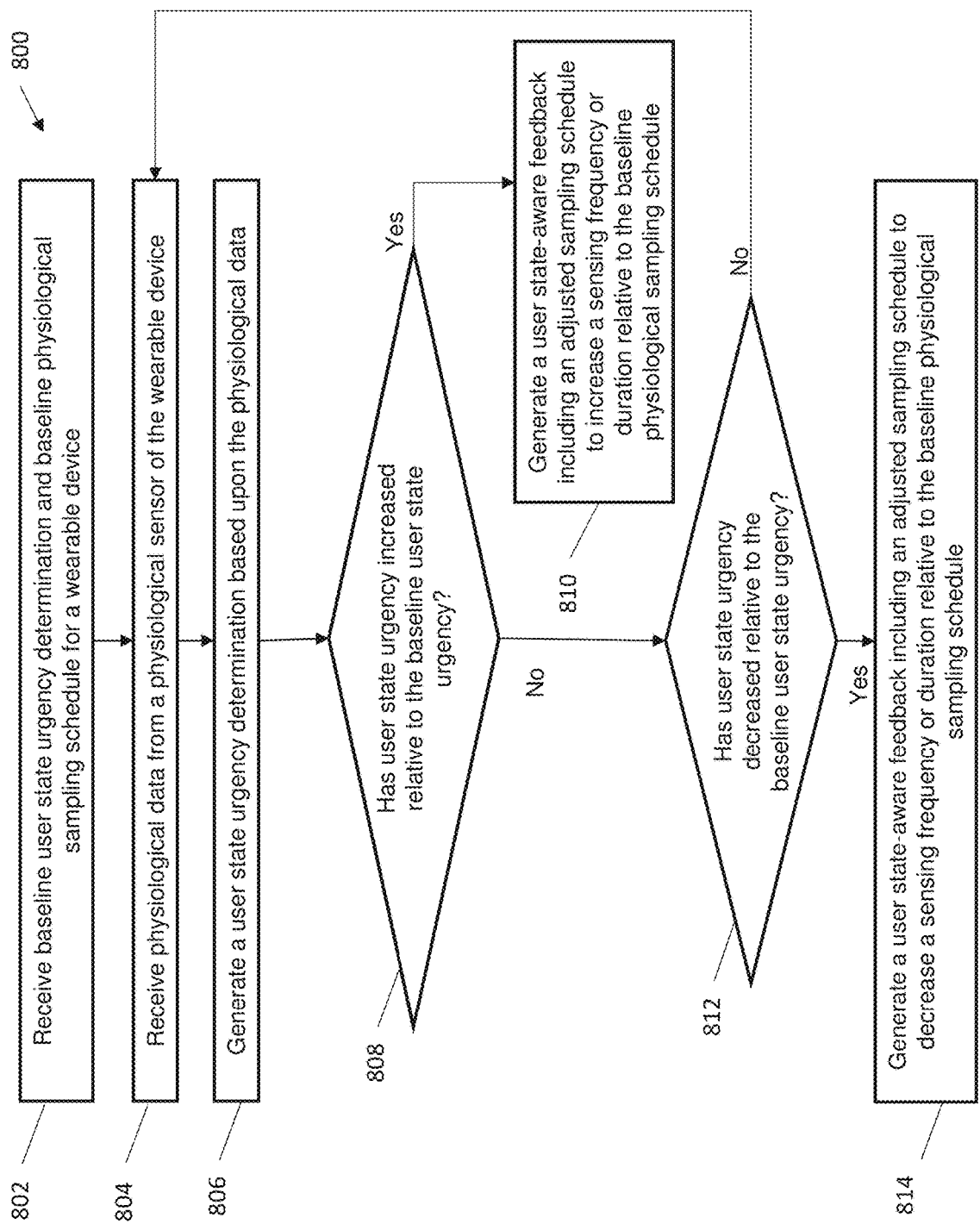
FIG. 8 depicts a flow diagram illustrating an exemplary method according to embodiments of the present invention.

FIG. 8 depicts a flow diagram illustrating an exemplary method 800 for generating a user state-aware feedback according to embodiments of the present invention. The method 800 includes, as shown at block 802, receiving a baseline user state-urgency determination and baseline physiological sampling schedule for a wearable device. In some embodiments of the invention, the baseline user state-urgency determination and baseline physiological sampling schedule are generated in a learning phase. The method 800 also includes, as shown at block 804, receiving physiological data from a physiological sensor of the wearable device. The method 800 also includes, as shown at block 806, generating a user-state urgency estimation based upon the physiological data. The method 800 asks, at decision block 808, whether the user state urgency estimation has increased relative to baseline user state urgency determination. Responsive to a determination that the user state urgency determination has increased relative to the baseline user state urgency, the method 800 proceeds to block 810 and generates a user state-aware feedback including an adjusted sampling schedule to increase a sensing frequency or duration relative to the baseline physiological sampling schedule. Responsive to a determination that the user state urgency determination has increased relative to the baseline user state urgency, the method 800 can proceed to block 810 and generates an adjusted sampling schedule to increase a sensing frequency or duration. The adjusted sampling schedule can be based at least in part upon the user state-aware feedback. In some embodiments of the invention, the adjusted sampling schedule is based upon the user state-aware feedback and a context-aware feedback. Responsive to a determination at block 808 that the user state urgency has not increased relative to the baseline user state urgency, the method 800 can proceed to block 812 and asks whether the user state urgency has decreased relative to the baseline user state urgency. Responsive to a determination that the user state urgency has decreased, the method can proceed to block 814 and generates a user state-aware feedback including an adjusted sampling schedule to decrease a sensing frequency or duration relative to the baseline physiological sampling schedule. Responsive to a determination that the user state urgency has not decreased, the method can return to block 804.

Figure 9:
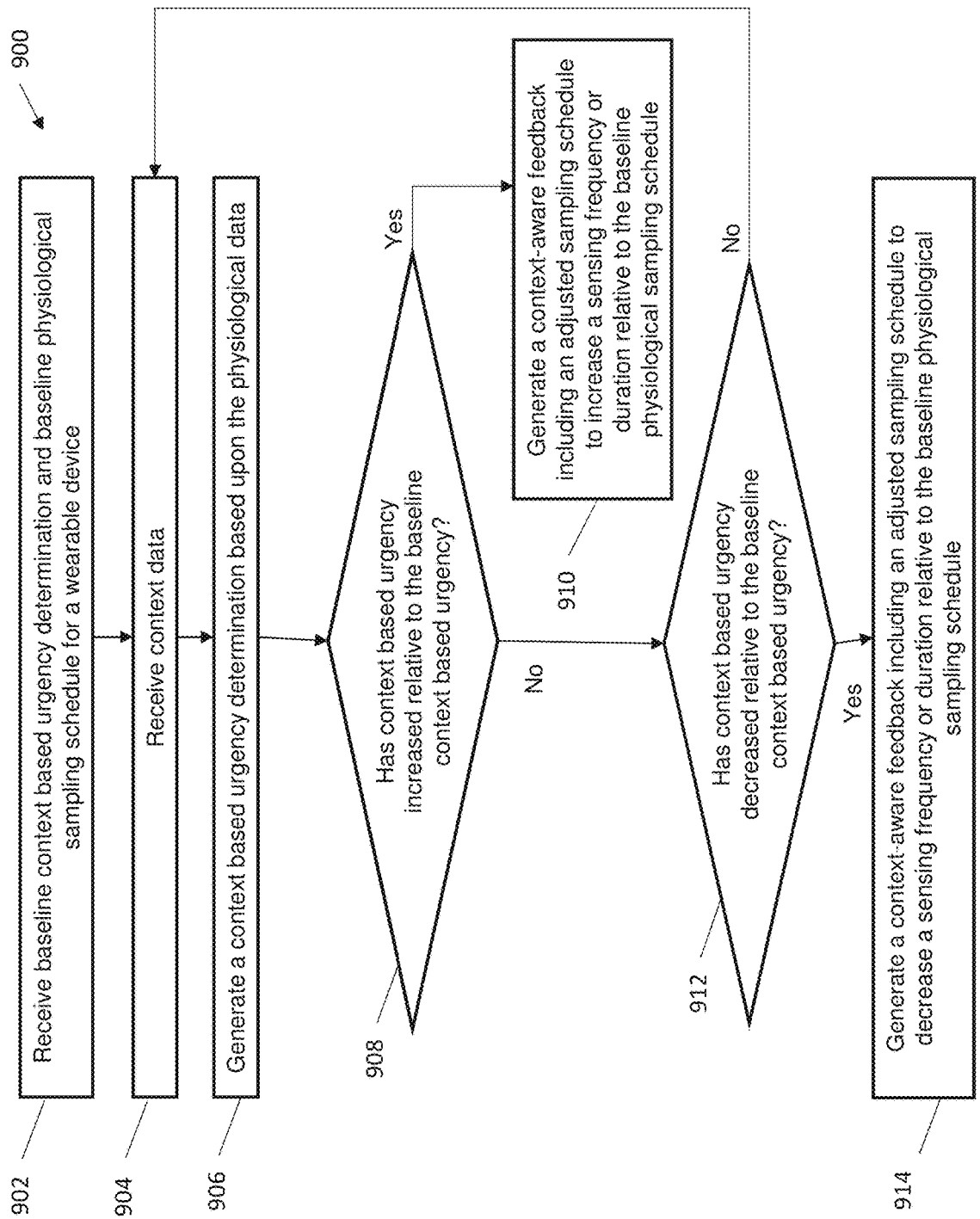
FIG. 9 depicts a flow diagram illustrating an exemplary method according to embodiments of the present invention.

FIG. 9 depicts a flow diagram illustrating an exemplary method 900 for generating a context-aware feedback according to embodiments of the present invention. The method 900 includes, as shown at block 902, receiving a baseline context based urgency determination and baseline physiological sampling schedule for a wearable device. In some embodiments of the invention, the baseline context based urgency determination and baseline physiological sampling schedule are generated in a learning phase. The method 900 also includes, as shown at block 904, receiving context data, for instance from a calendar, a location based sensor, or from the Internet. The method 900 also includes, as shown at block 906, generating a context based urgency estimation based upon the physiological data. The method 900 asks, at decision block 908, whether the context based urgency estimation has increased relative to baseline user state urgency determination. Responsive to a determination that the context based determination has increased relative to the baseline context based urgency, the method 900 proceeds to block 910 and generates a context-aware feedback including an adjusted sampling schedule to increase a sensing frequency or duration relative to the baseline physiological sampling schedule. Responsive to a determination that the context based urgency has increased relative to the baseline context based urgency, the method 900 can proceed to block 910 and generates an adjusted sampling schedule to increase a sensing frequency or duration. The adjusted sampling schedule can be based at least in part upon the context-aware feedback. In some embodiments of the invention, the adjusted sampling schedule is based upon the context-aware feedback and a user state-aware feedback. Responsive to a determination at block 908 that the user state urgency has not increased relative to the baseline user state urgency, the method 900 can proceed to block 912 and asks whether the user state urgency has decreased relative to the baseline user state urgency. Responsive to a determination that the context based urgency has decreased, the method can proceed to block 914 and generates a context-aware feedback including an adjusted sampling schedule to decrease a sensing frequency or duration relative to the baseline physiological sampling schedule. Responsive to a determination that the context based urgency has not decreased, the method can return to block 904.

Example

A multi-faceted architecture according to embodiments of the invention was used in a stress monitoring application. For stress monitoring, a wearable device including a heart rate monitor was used in a conventional timer-based sampling schedule and compared to a multi-faceted sampling regulator including quality-aware and user state-aware feedback according to embodiments of the invention. Prior to testing, a baseline was determined. Stress level was monitored for six hours and during that time user feedback concerning stress levels was collected.

FIGS. 10A, 10B, and 10C depict the results. FIG. 10A depicts measured motion level, as determined by an accelerometer over the tested time period. FIG. 10B depicts the measured stress level of the measured device. FIG. 10B also depicts the user indicated stress level for time periods bounded by vertical dashed lines (No stress (NS), no data (ND), or stress (S)). FIG. 10C depicts of the sampling schedule of the conventional timer based system (top) versus the multi-faceted system according to an embodiment of the invention. The conventional system sampled with physiological sensors for 150 minutes (39.5%) and obtained 39 minutes (45.9%) of stress coverage. The multi-faceted system, on the other hand, sampled for 168 minutes (44.2%) and obtained 85 minutes (100%) of stress coverage. Thus, the multi-faceted sampling regulator achieved superior coverage relative to the conventional timer-based system with a similar energy consumption.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments of the invention, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments of the invention, the practical application or technical improvement over technologies found in the marketplace, or to enable others of ordinary skill in the art to understand the embodiments described herein.

What is claimed is:

1. A processing system for physiological sensing in a wearable device, the system comprising a processor in communication with one or more types of memory, the processor configured to:
   generate a multi-faceted feedback for a user, wherein generating the multi-faceted feedback comprises:
   generating a baseline physiological sampling schedule for a user;
   generating a quality-aware feedback of the user;
   generating a user-state-aware feedback of the user;
   polling a source external to the wearable device for contextual data associated with the user, the contextual data comprising at least one of calendar data and email data; and
   generating a context-aware feedback of the user, the context-aware feedback indicating a historically stressful context for the user based in part on a current location of the user and the polled contextual data;
   generate an adjusted physiological sampling schedule for the user based at least in part upon the multi-faceted feedback, the adjusted physiological sampling schedule comprising at least a first period of time during which sampling is suspended due to the quality-aware feedback indicating that a level of movement of the user is sufficiently high to cause interference in the physiological sensing and a second period of time during which sampling is increased due to the polled contextual data indicative of the historically stressful context for the user; and
   adjust a sampling frequency of a physiological sensor of the wearable device based on the adjusted physiological sampling schedule.

2. The processing system of claim 1, wherein generating the multi-faceted feedback comprises generating an energy-aware feedback of the user.

3. The processing system of claim 1, wherein generating the quality-aware feedback comprises:
   receiving an active indication from a physiological sensor on the wearable device;
   receiving a real-time low-power motion sensor data from the wearable device;
   generating an interference level estimation for the physiological sensor based upon the real-time low-power motion sensor data; and
   comparing the interference level estimation to an interference threshold.

4. The processing system of claim 3, wherein the processor is further configured to reduce physiological sensing responsive to the comparison.

5. The processing system of claim 1, wherein generating the user state-aware feedback comprises:
   receiving a baseline user state urgency determination;
   receiving physiological data from a physiological sensor of the wearable device;
   generating a user state urgency determination based at least in part upon the physiological data; and
   comparing the user state urgency determination to the baseline user state urgency determination.

6. The processing system of claim 5, wherein the processor is further configured to modify a physiological sensing frequency or duration responsive to the comparison.

7. The processing system of claim 1, wherein generating the context-aware feedback comprises:
   receiving a baseline context based urgency determination;
   receiving context data;
   generating a context based urgency determination based at least in part upon the physiological data; and
   comparing the context based urgency determination to the baseline context based urgency determination.

8. A computer-implemented method for physiological sensing in a wearable device, the method comprising:

generating, using a processor, a multi-faceted feedback for a user, wherein generating the multi-faceted feedback comprises:
  generating a baseline physiological sampling schedule for a user;
  generating a quality-aware feedback of the user;
  generating a user-state-aware feedback of the user;
  polling a source external to the wearable device for contextual data associated with the user, the contextual data comprising at least one of calendar data and email data; and
  generating a context-aware feedback of the user, the context-aware feedback indicating a historically stressful context for the user based in part on a current location of the user and the polled contextual data;
generating, using a processor, an adjusted physiological sampling schedule for the user based at least in part upon the multi-faceted feedback, the adjusted physiological sampling schedule comprising at least a first period of time during which sampling is suspended due to the quality-aware feedback indicating that a level of movement of the user is sufficiently high to cause interference in the physiological sensing and a second period of time during which sampling is increased due to the polled contextual data indicative of the historically stressful context for the user; and
adjusting a sampling frequency of a physiological sensor of the wearable device based on the adjusted physiological sampling schedule.

9. The computer implemented method of claim 8, wherein generating the multi-faceted feedback comprises generating an energy-aware feedback of the user.

10. The computer implemented method of claim 8, wherein generating the quality-aware feedback comprises:
  receiving an active indication from a physiological sensor on the wearable device;
  receiving a real-time low-power motion sensor data from the wearable device;
  generating an interference level estimation for the physiological sensor based at least in part upon the real-time low-power motion sensor data; and
  comparing the interference level estimation to an interference threshold.

11. The computer implemented method of claim 10, further comprising reducing physiological sensing responsive to the comparison.

12. The computer implemented method of claim 8, wherein generating the user state-aware feedback comprises:
  receiving a baseline user state urgency determination;
  receiving physiological data from a physiological sensor of the wearable device;
  generating a user state urgency determination based at least in part upon the physiological data; and
  comparing the user state urgency determination to the baseline user state urgency determination.

13. The computer implemented method of claim 12, further comprising modifying a physiological sensing frequency or duration responsive to the comparison.

14. The computer implemented method of claim 8, wherein generating the context-aware feedback comprises:
  receiving a baseline context based urgency determination;
  receiving context data;
  generating a context based urgency determination based at least in part upon the physiological data; and
  comparing the context based urgency determination to the baseline context based urgency determination.

15. A non-transitory computer program product for physiological sensing in a wearable device, the computer program product comprising:
  a computer readable storage medium having program instructions embodied therewith, wherein the instructions are executable by a processor to cause the processor to perform a method comprising:
  generating a multi-faceted feedback for a user, wherein generating the multi-faceted feedback comprises:
    generating a baseline physiological sampling schedule for a user;
    generating a quality-aware feedback of the user;
    generating a user-state-aware feedback of the user;
    polling a source external to the wearable device for contextual data associated with the user, the contextual data comprising at least one of calendar data and email data; and
    generating a context-aware feedback of the user, the context-aware feedback indicating a historically stressful context for the user based in part on a current location of the user and the polled contextual data;
  generating an adjusted physiological sampling schedule for the user based at least in part upon the multi-faceted feedback, the adjusted physiological sampling schedule comprising at least a first period of time during which sampling is suspended due to the quality-aware feedback indicating that a level of movement of the user is sufficiently high to cause interference in the physiological sensing and a second period of time during which sampling is increased due to the polled contextual data indicative of the historically stressful context for the user; and
  adjust a sampling frequency of a physiological sensor of the wearable device based on the adjusted physiological sampling schedule.

\* \* \* \* \*